US011679239B2

(12) United States Patent
Yang et al.

(10) Patent No.: US 11,679,239 B2
(45) Date of Patent: Jun. 20, 2023

(54) DOUBLE-LAYER CRYOGENIC INFLATABLE BALLOON

(71) Applicant: AccuTarget MediPharma (Shanghai) Co., LTD., Shanghai (CN)

(72) Inventors: Chi Yang, Shanghai (CN); Zhaohua Chang, Shanghai (CN)

(73) Assignee: AccuTarget MediPharma (Shanghai) Co., LTD., Shanghai (CN)

( * ) Notice: Subject to any disclaimer, the term of this patent is extended or adjusted under 35 U.S.C. 154(b) by 0 days.

(21) Appl. No.: 17/626,128

(22) PCT Filed: Feb. 24, 2021

(86) PCT No.: PCT/CN2021/077683
§ 371 (c)(1),
(2) Date: Jan. 11, 2022

(87) PCT Pub. No.: WO2021/248939
PCT Pub. Date: Dec. 16, 2021

(65) Prior Publication Data
US 2022/0273917 A1    Sep. 1, 2022

(30) Foreign Application Priority Data

Jun. 9, 2020 (CN) .......................... 202010520694.7
Jun. 9, 2020 (CN) .......................... 202021050075.8

(51) Int. Cl.
*A61M 25/10*    (2013.01)
*A61B 18/02*    (2006.01)
(Continued)

(52) U.S. Cl.
CPC ......... *A61M 25/1011* (2013.01); *A61B 18/02* (2013.01); *A61M 29/02* (2013.01);
(Continued)

(58) Field of Classification Search
CPC ............ A61B 18/02; A61B 2018/0287; A61B 2018/0262; A61B 2018/00916;
(Continued)

(56) References Cited

U.S. PATENT DOCUMENTS 6,517,533 B1    2/2003 Swaminathan
10,058,371 B2   8/2018 Sara et al.
(Continued)

FOREIGN PATENT DOCUMENTS

CN    106102816 A    11/2016
CN    206414506 U     8/2017
(Continued)

OTHER PUBLICATIONS

International Search Report, issued in PCT/CN2021/077683, dated May 14, 2021.
(Continued)

*Primary Examiner* — Ronald Hupczey, Jr.
(74) *Attorney, Agent, or Firm* — Zhu Lehnhoff LLP

(57) ABSTRACT

The present invention provides a double-layer cryogenic inflatable balloon including an inflatable balloon assembly and a cryogenic balloon assembly. The inflatable balloon assembly includes an inflatable balloon, an outer catheter and a liquid-filling cavity provided with a liquid-filling chamber, the inflatable balloon, the outer catheter and the liquid-filling cavity being communicated with each other. The cryogenic balloon assembly includes a cryogenic balloon, an inner catheter and a fluid-diverting cavity provided with a gas return chamber as well as a gas inlet pipe and an inflation assembly, the cryogenic balloon, the inner catheter and the fluid-diverting cavity being communicated with each other, wherein the cryogenic balloon is located in the inflatable balloon, and the inner catheter is located in the outer catheter. The fluid-diverting cavity is further provided with (Continued)

a gas return channel, a liquid-filling channel, and a cork chamber, wherein the gas return channel has one end communicated with the gas return chamber and the other end communicated with the cork chamber. The liquid-filling channel has one end communicated with the cork chamber and the other end communicated with the liquid-filling chamber. The cork chamber is communicated with a gas return joint, and is internally provided with an adjustment structure. The fluid-diverting cavity is provided with a gas inlet chamber, and the gas inlet pipe penetrates through the cryogenic balloon, the inner catheter and the fluid-diverting cavity, the gas inlet pipe having one end located in the cryogenic balloon and the other end communicated with the gas inlet chamber. The gas inlet chamber is communicated with the inflation assembly, and the inflation assembly is used to input a refrigerant gas into the cryogenic balloon through a pipe.

17 Claims, 11 Drawing Sheets

(51) Int. Cl.
*A61M 29/02* (2006.01)
*A61B 18/00* (2006.01)

(52) U.S. Cl.
CPC ............. *A61B 2018/00023* (2013.01); *A61B 2018/00255* (2013.01); *A61B 2018/00577* (2013.01); *A61B 2018/00744* (2013.01); *A61B 2018/0212* (2013.01)

(58) Field of Classification Search
CPC .. A61B 2018/00958; A61M 25/10185; A61M 39/223
See application file for complete search history.

(56) References Cited

U.S. PATENT DOCUMENTS

| | | | |
|---|---|---|---|
| 2002/0007180 A1 | 1/2002 | Wittenberger et al. | |
| 2002/0183731 A1* | 12/2002 | Holland | A61B 18/02 606/21 |
| 2009/0281533 A1 | 11/2009 | Ingle et al. | |
| 2010/0069900 A1* | 3/2010 | Shirley | A61B 18/02 604/509 |
| 2011/0190751 A1 | 8/2011 | Ingle et al. | |

FOREIGN PATENT DOCUMENTS

| | | |
|---|---|---|
| CN | 107411815 A | 12/2017 |
| CN | 109646106 A | 4/2019 |
| CN | 110051420 A | 7/2019 |
| CN | 209826948 U | 12/2019 |
| CN | 111631808 A | 9/2020 |

OTHER PUBLICATIONS

Written Opinion, issued in PCT/CN2021/077683, dated May 14, 2021.

* cited by examiner

DOUBLE-LAYER CRYOGENIC INFLATABLE BALLOON

BACKGROUND OF THE INVENTION

Field of the Invention

The present invention relates to the technical field of medical instruments, and more specifically, to a double-layer cryogenic inflatable balloon.

Description of the Prior Art

The airways, esophagus, or blood vessels may have stenosis due to a variety of causes. Current treatments for these cavities with stenosis include using balloon inflation, stents, cryogenic ablation and thermal ablation. Treatments using balloon inflation and stents focus on physical inflation of stenosis sites, while treatments using cryogenic ablation and thermal ablation focus on the treatment of lesions in stenosis sites. Taking the treatment for the stenosis airway as an example, in order to reduce the hyperplasia of granulation tissues and the formation of scar contracture and to avoid long-term complications, treatments with mild stimulation on local tissues should be chosen clinically, wherein in terms of the degree of stimulation generated on local tissues, the strongest is the metal stents, followed by the silicone stents and thermal ablations such as lasers and electric burns, the balloon inflation and the cryotherapy with the lightest stimulation. The process of the treatment using the thermal ablation technique may itself cause heavier and wider range of damages to the airway, which results in the hyperplasia of granulation tissue and the formation of scar contracture severely, thereby leading to high rates of complications and recurrence. For the treatment using the balloon inflation, the operation is simple and long-term complications are fewer, but the resulted effects are not long-lasting and the recurrence is easy to occur. Compared with the treatment using the thermal ablation, the cryotherapy does not promote the hyperplasia of granulation tissue and is not easy to cause cartilage damage, so the cryotherapy may avoid damages to airway walls and rarely causes complications of airway softening and collapse; this treatment method is a simple and safe treatment method and can be adapted to all types of stenosis cases. However, the existing airway cryogenic products are limited to the treatment for a single point, and the surgical operation is particularly cumbersome and time-consuming for the treatment of large airway stenosis.

A unitary treatment is difficult to achieve satisfactory results, so a combination of methods is often required clinically, e.g., a treatment of combining the balloon inflation with cryotherapy, wherein the collagen deposition in the position where the airway is damaged can be significantly reduced by the balloon inflation and then supplemented by local cryotherapy, so as to inhibit the formation of scar contracture. However, this treatment method is performed by first using the conventional inflatable balloon and then using the flexible cryogenic probe (single-point treatment), which results in cumbersome operation and incomplete coverage. Therefore, achieving the balloon inflation and the balloon cryotherapy on a unitary mechanical instrument has a significant clinical value.

Clinically, the saline is typically used for the balloon inflation, and the inflation using liquids is more quick and safe as compared with the inflation using gases as the gas has compressibility while the liquid is almost incompressible; therefore, the balloon inflation using gases requires more injections and longer time. In addition, in the event of a gas leak in the balloon, often swelling organs, embolism or suffocation may be caused to occur, which may bring a life risk to the patient, but the leakage of saline will not bring in such results.

The existing inflatable balloon does not have cryogenic functions, and may only inflate the stenosis sites temporarily and unitarily, thereby being unable to treat the lesions or inhibiting the complications. The existing cryogenic balloon usually only has the cryogenic functions, which cannot achieve the inflation under a high pressure. If a cryogenic structure is simply added into the existing inflatable balloon, residual liquids in the balloons and gas inlet pipes can cause ice jams that can occur easily during cryotherapy and further cause poor cryogenic effects (due to the absorption of a part of cryogenic amount by the residual liquids) when the balloon is filled with liquids to be inflated and the liquids are drained.

SUMMARY OF THE INVENTION

In view of the problems in background, the present invention provides a double-layer cryogenic inflatable balloon, which includes:

an inflatable balloon assembly, including an inflatable balloon, an outer catheter and a liquid-filling cavity, the liquid-filling cavity being provided with a liquid-filling chamber, the inflatable balloon being communicated with the liquid-filling chamber through the outer catheter;

a cryogenic balloon assembly, including a cryogenic balloon, an inner catheter, a fluid-diverting cavity, a gas inlet pipe and an inflation assembly, the cryogenic balloon being located in the inflatable balloon, the inner catheter being located in the outer catheter, the fluid-diverting cavity being provided with a gas return chamber, the cryogenic balloon being communicated with the gas return chamber through the inner catheter;

wherein the fluid-diverting cavity is further provided with a gas return channel, a liquid-filling channel and a cork chamber, the gas return channel having one end communicated with the gas return chamber and the other end communicated with the cork chamber; the liquid-filling channel has one end communicated with the cork chamber and the other end communicated with the liquid-filling chamber; the cork chamber is communicated with a gas return joint, and is internally provided with an adjustment structure for achieving connection and disconnection between the gas return channel and the gas return joint, between the gas return joint and the liquid-filling channel and between the gas return channel and the liquid-filling channel;

the fluid-diverting cavity is further provided with a gas inlet chamber, and the gas inlet pipe penetrates through the cryogenic balloon, the inner catheter and the fluid-diverting cavity, the gas inlet pipe having one end located in the cryogenic balloon and the other end communicated with the gas inlet chamber; the gas inlet chamber is further communicated with the inflation assembly, and the inflation assembly is used to input a refrigerant gas into the cryogenic balloon through the gas inlet chamber and the gas inlet pipe.

Preferably, the liquid-filling cavity is disposed on an end of the fluid-diverting cavity facing towards the inner catheter, the end of the fluid-diverting cavity facing towards the inner catheter is provided with the gas return chamber, and the inner catheter extends out of the outer catheter to pass through the liquid-filling chamber and is then communicated with the gas return chamber.

Preferably, the gas inlet chamber is disposed on an end of the fluid-diverting cavity deviated from the inner catheter, a gas inlet hole is disposed between the gas inlet chamber and the gas return chamber, the other end of the gas inlet pipe extends out of the inner catheter to pass through the liquid-filling chamber and the gas return chamber in sequence and is then in sealed connection with the gas inlet hole.

Preferably, an end of the gas inlet pipe located in the cryogenic balloon is connected with a spiral gas inlet pipe, and a gas outlet hole is formed in the spiral gas inlet pipe.

Preferably, a plurality of the gas outlet holes are formed uniformly in the spiral gas inlet pipe in an axial direction and a radial direction thereof.

Preferably, the inflation assembly includes a gas bottle and a gas bottle opening component, and the gas bottle is connected to the gas inlet chamber through the gas bottle opening component.

Preferably, the gas bottle opening component includes a valve body, a hollow ejector pin and a pushing rod assembly, and the valve body has one end connected to the gas inlet chamber and the other end connected with a bottle mouth of the gas bottle; the hollow ejector pin is movably mounted in the valve body, with one end located in the gas inlet chamber and the other end abutting against a sealing mechanism in the bottle mouth; one end of the pushing rod assembly is connected with the hollow ejector pin, and may drive an axis of the hollow ejector pin to move to eject off the sealing mechanism to extend into the gas bottle.

Preferably, the inflation assembly is mounted on the fluid-diverting cavity through a casing assembly.

Preferably, the casing assembly includes a left semi-casing and a right semi-casing that are covered on the inflation assembly symmetrically in the radial direction, and a rear lid covering on a side of the inflation assembly deviated from the fluid-diverting cavity; one ends of the left semi-casing and a right semi-casing are connected onto the fluid-diverting cavity, and the rear lid is connected onto the other ends of the left semi-casing and a right semi-casing.

Preferably, inner side walls of the left semi-casing and a right semi-casing are provided with a limiting plate clamped on the gas bottle opening component.

Preferably, the rear lid is provided with a vent hole.

Preferably, the adjustment structure is of a three-pass cork valve, and the three-pass cork valve is rotated to achieve the connection and disconnection between the gas return channel and the gas return joint and between the gas return joint and the liquid-filling channel.

Preferably, the cork post is further connected with a handle for driving the cork post to rotate, and the handle is provided with an indication sign for indicating the connection between the gas return channel and the gas return joint, between the gas return joint and the liquid-filling channel and between the gas return channel and the liquid-filling channel.

Preferably, the fluid-diverting cavity is further provided with a pressure relief channel, and the pressure relief channel has one end communicated with the gas return chamber and the other end extending out of the fluid-diverting cavity and provided with a safety valve.

Preferably, the double-layer cryogenic inflatable balloon further includes a wire guiding pipe that penetrates through the cryogenic balloon, the inner catheter, the liquid-filling chamber and the gas return chamber; one end of the wire guiding pipe extends into the cryogenic balloon while being connected with the front ends of the cryogenic balloon and the inflatable balloon, and the other end of the wire guiding pipe is extracted from a wire guiding hole in the fluid-diverting cavity.

Due to the adoption of the above technical solutions, the present invention, as compared with the prior art, has the following advantages and active effects:

The double-layer cryogenic inflatable balloon provided by the present invention may realize the balloon inflation and the cryogenic treatment simultaneously, and separates the liquid space from the refrigerant space by the double-layer balloon structure with the out-built inflatable balloon and the in-built cryogenic balloon, so that the liquid-filling inflation and the cryogenic treatment may be realized safely and effectively, thereby preventing the blockade and poor cryogenic effects caused by mixing the inflation liquid with the refrigerant gas.

BRIEF DESCRIPTION OF THE DRAWINGS

Combined with the drawings, the above and other features and advantages of the present invention can be better understood through the detailed instructions described below, wherein.

DESCRIPTION OF SYMBOLS

Figure 1:
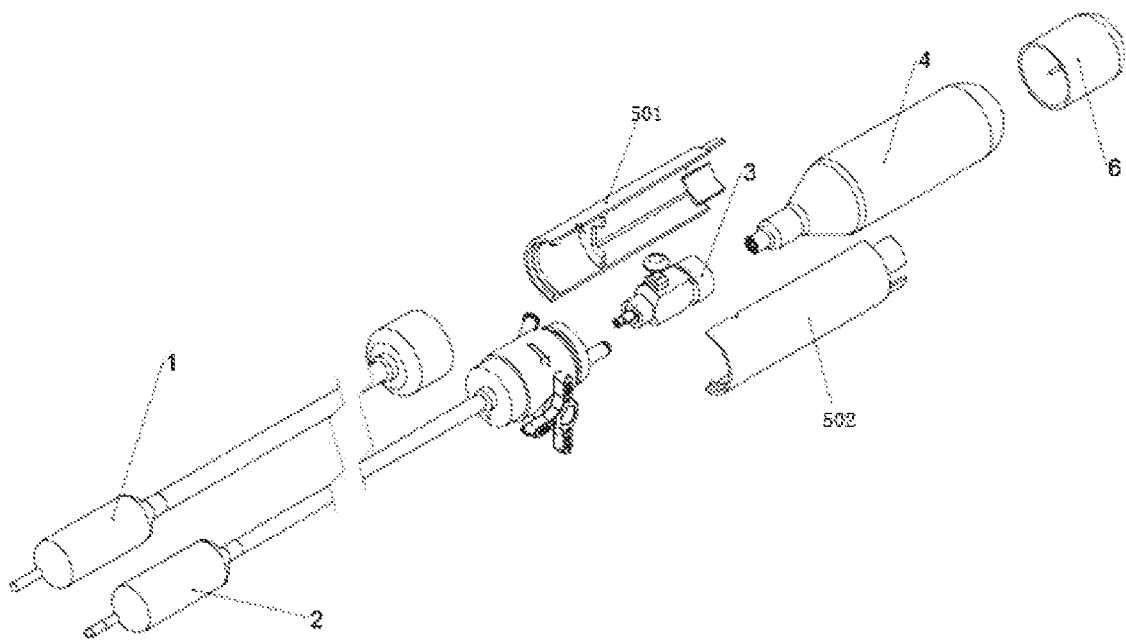
FIG. 1 is a split diagram of the double-layer cryogenic inflatable balloon provided by the present invention.

1—inflatable balloon assembly, 11—inflatable balloon, 12—outer catheter, 13—fluid-filling cavity, 14—fluid-filling chamber, 2—cryogenic balloon assembly, 21—cryogenic balloon, 22—inner catheter, 23—fluid-diverting cavity, 231—gas return chamber, 232—gas inlet chamber, 233—gas return channel, 234—liquid-filling channel, 235—gas inlet hole, 236—wire guiding hole, 237—pressure relief channel, 238—cork chamber, 239—indication sign, 24—gas inlet pipe, 241—spiral gas inlet pipe, 242—gas outlet hole, 25—wire guiding pipe, 251—wire guiding pipe head, 26—wire guiding outlet, 27—three-pass cork valve, 271—handle, 272—cork post, 28—gas return joint, 29—safety valve, 3—gas bottle opening component, 31—valve body, 32—button, 33—pushing rod, 34—hollow ejector pin, 4—gas bottle component, 41—bottle mouth, 42—gas bottle, 5—casing, 501—left casing, 502—right casing, 51—limiting ring, 52—limiting plate, 521, 62—vent hole, 53—thread portion, 54, 61—reinforcing rib, 6—rear lid.

DESCRIPTION OF THE PREFERRED EMBODIMENTS

With reference to the drawings showing the embodiments of the present invention, the present invention will be described in more detail below. However, the present invention may be implemented in many different forms and should not be interpreted as being subject to the limitations of the embodiment proposed here. In contrast, these embodiments are proposed in order to achieve full and complete disclosure, and to enable those skilled in the art to fully understand the scope of the present invention. In these figures, for clarity, the dimensions and relative dimensions of the layers and areas may have been enlarged.

It should be noted that all the directional indications (such as up, down, left, right, front, and back) in the embodiments of the present invention are only used to explain the relative positional relationship, motion situation and the like between the components under a specific attitude (as shown in the drawings), and if the specific attitude changes, then the directional indications also change accordingly.

With reference to FIGS. 1 to 14, the present invention provides a double-layer cryogenic inflatable balloon including an inflatable balloon assembly 1 and a cryogenic balloon assembly 2; the inflatable balloon assembly 1 includes an inflatable balloon 11, an outer catheter 12 and a liquid-filling cavity 13, the liquid-filling cavity 13 being provided with a liquid-filling chamber 14, the inflatable balloon 11 being communicated with the liquid-filling chamber 14 through the outer catheter 12; the cryogenic balloon assembly 2 includes a cryogenic balloon 21, an inner catheter 22, a fluid-diverting cavity 23, a gas inlet pipe 24 and an inflation assembly, the cryogenic balloon being located in the inflatable balloon 11, the inner catheter 22 being located in the outer catheter 12, the fluid-diverting cavity 23 being provided with a gas return chamber 231, the cryogenic balloon 21 being communicated with the gas return chamber 231 through the inner catheter 22; the fluid-diverting cavity 23 is further provided with a gas return channel 233, a liquid-filling channel 234 and a cork chamber 238, the gas return channel 233 having one end communicated with the gas return chamber 231 and the other end communicated with the cork chamber 238; the liquid-filling channel 234 has one end communicated with the cork chamber 238 and the other end communicated with the liquid-filling chamber 234; the cork chamber 238 is communicated with a gas return joint 28, and the cork chamber 238 is internally provided with an adjustment structure for achieving connection and disconnection between the gas return channel 233 and the gas return joint 28, between the gas return joint 28 and the liquid-filling channel 234 and between the gas return channel 233 and the liquid-filling channel 234; the fluid-diverting cavity 23 is provided with a gas inlet chamber 232, and the gas inlet pipe 24 penetrates through the cryogenic balloon 21, the inner catheter 22 and the fluid-diverting cavity 23, the gas inlet pipe 24 having one end located in the cryogenic balloon 21 and the other end communicated with the gas inlet chamber 232; the gas inlet chamber 232 is communicated with the inflation assembly, and the inflation assembly inputs a refrigerant gas into the cryogenic balloon 21 through the gas inlet chamber 232 and the gas inlet pipe 24.

When in use, the adjustment structure is adjusted such that the gas return joint 28 is communicated with the liquid-filling channel 234 and the gas return joint 28 is not communicated with the gas return pipe 233, and the gas return joint 28 is communicated with an external liquid-filling gun to inject a saline into the inflatable balloon 11 through the gas return joint 28, the cork chamber 238, the liquid-filling pipe 234, the liquid-filling chamber 14 and a gap between the outer catheter 12 and the inner catheter 22 in sequence by the liquid-filling gun so that the inflatable balloon 11 begins to inflate, and then the saline in the inflatable balloon 11 is drained by the liquid-filling gun after the inflation is completed; then, the adjustment structure is adjusted again such that the gas return joint 28 is communicated with the gas return pipe 233 and the gas return joint 28 is not communicated with the liquid-filling channel 234, and the inflation assembly is initiated to charge a refrigerant into the cryogenic balloon 21 through the gas inlet pipe 24.

The double-layer cryogenic inflatable balloon provided by the present invention may realize the balloon inflation and the cryotherapy simultaneously, and separates a liquid space from a refrigerant space by the double-layer balloon structure with the out-built inflatable balloon and the in-built cryogenic balloon, so that the liquid-filling inflation and the cryotherapy may be realized safely and effectively for a single product, thereby preventing the blockade and poor cryogenic effects caused by mixing the inflatable liquid with the refrigerant gas.

Figure 2:
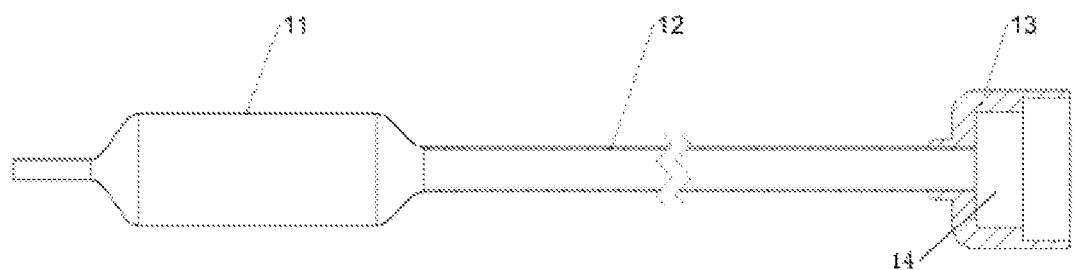
FIG. 2 is a structural diagram of an inflatable balloon assembly in the present invention.
Figure 3:
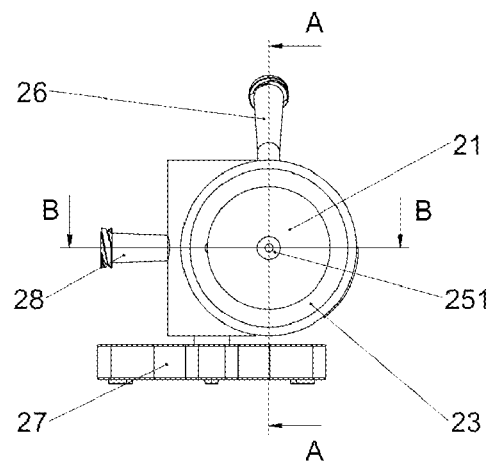
FIG. 3 is an axial diagram of a cryogenic balloon assembly in the present invention.

In the present embodiment, as shown in FIG. 2, a rear end of the inflatable balloon 11 is connected and communicated with a front end of the outer catheter 12, and the connection therebetween is sealed, e.g., specifically by a sealant and a sealing ring, etc.; a rear end of the outer catheter 12 is connected to the liquid-filling cavity 13 and is communicated with the liquid-filling chamber 14, and also the connection therebetween is sealed, e.g., specifically by a sealant and a sealing ring, etc. Further, the liquid-filling cavity 13 covers an end of the fluid-diverting cavity 23 facing towards the inner catheter 22, and forms the fluid-filling chamber 14 together with a front end surface of the fluid-diverting cavity 23; the connection between the liquid-filling cavity 13 and the fluid-diverting cavity 23 is sealed, e.g., specifically by a sealant and a sealing ring, etc.

Preferably, the inflatable balloon 11 is a multi-stage inflatable balloon; in other words, the greater the liquid-filling pressure is, the larger the corresponding diameter of the inflatable balloon 11 is.

Figure 4:
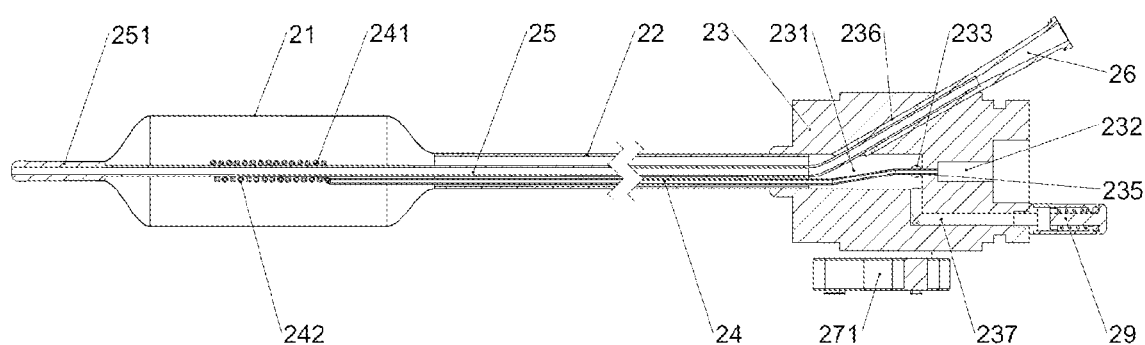
FIG. 4 is an axial cross-section diagram taken from A-A of the cryogenic balloon assembly in the present invention.

In the present embodiment, as shown in FIG. 4, a rear end of the cryogenic balloon 21 is connected and communicated with a front end of the inner catheter 22, and the connection therebetween is sealed, e.g., specifically by a sealant and a sealing ring, etc.; a rear end of the inner catheter 22 is connected to the fluid-diverting cavity 23. An end of the fluid-diverting cavity 23 facing towards the inner catheter 22 is provided with a gas return chamber 231, the inner catheter 22 protrudes out of the outer catheter 12 and then passes through the liquid-filling chamber 14 to be inserted into the gas return chamber 231 for achieving communication; the connection therebetween is sealed, e.g., by a sealant and a sealing ring, etc., as shown in FIG. 4.

The diameter of the cryogenic balloon 21 after being inflated should be equal to or slightly greater than the diameter of the inflatable balloon 11 in a maximum liquid-filling pressure, so as to ensure that the cryogenic balloon 21 contacts an inner wall of the inflatable balloon 11 all the time in a cryogenic state.

In the present embodiment, the gas inlet chamber 232 is disposed on an end of the fluid-diverting cavity 23 deviated from the inner catheter 22, and a gas inlet hole 235 is disposed co-axially between the gas inlet chamber 232 and the gas return chamber 231; the other end of the gas inlet pipe 24 protrudes out of the inner catheter 22 and then passes through the liquid-filling chamber 14 and the gas return chamber 231 in sequence to be inserted into the gas inlet hole 235 for achieving communication; the connection therebetween is sealed, e.g., by a sealant and a sealing ring, etc.

In the present embodiment, an end of the gas inlet pipe 24 located in the cryogenic balloon 21 is connected with a spiral gas inlet pipe 241, and a gas outlet hole 242 is arranged on the spiral gas inlet pipe 241. Further, a plurality of the gas outlet holes 242 are formed uniformly in the spiral gas inlet pipe 241 in an axial direction and a radial direction thereof. In the present embodiment, through the design of the above structure, the refrigerant gas is sprayed to the cryogenic balloon 21 uniformly in the axial and radial directions, so that a surface temperature of the cryogenic balloon 21 is even.

In the present embodiment, the adjustment structure is of a three-pass cork valve 27; the three-pass cork valve 27 is rotated to achieve the connection and disconnection between the gas return channel 233 and the gas return joint 28 and between the gas return joint 28 and the liquid-filling channel 234.

Figure 5:
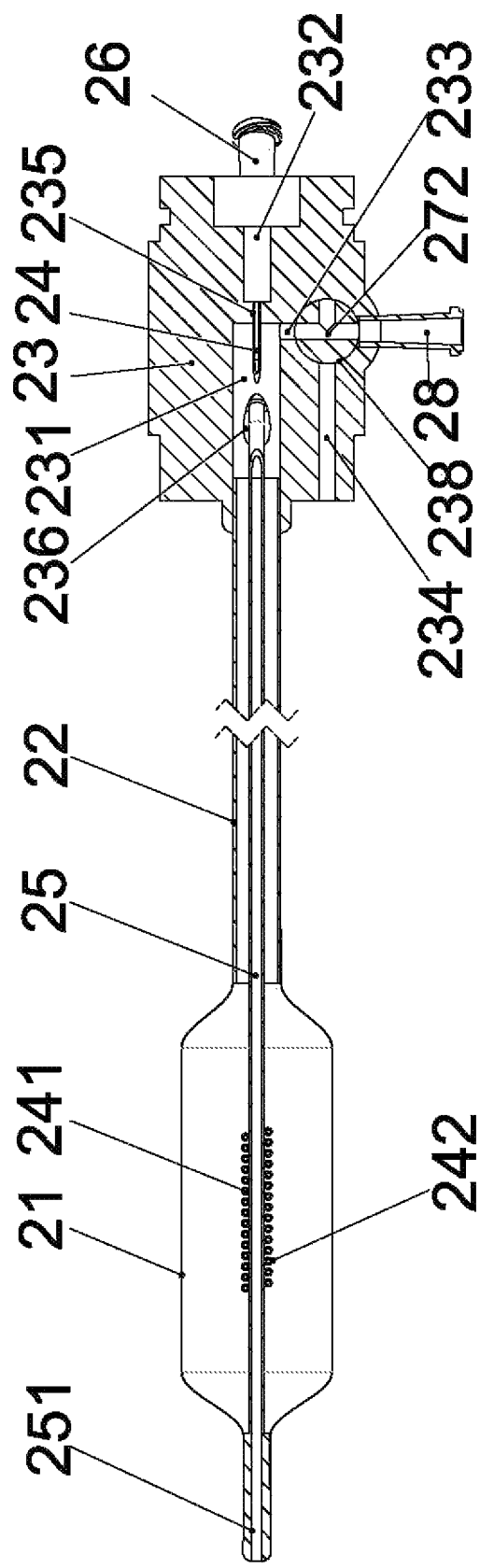
FIG. 5 is an axial cross-section diagram taken from B-B of the cryogenic balloon assembly in the present invention.
Figure 6:
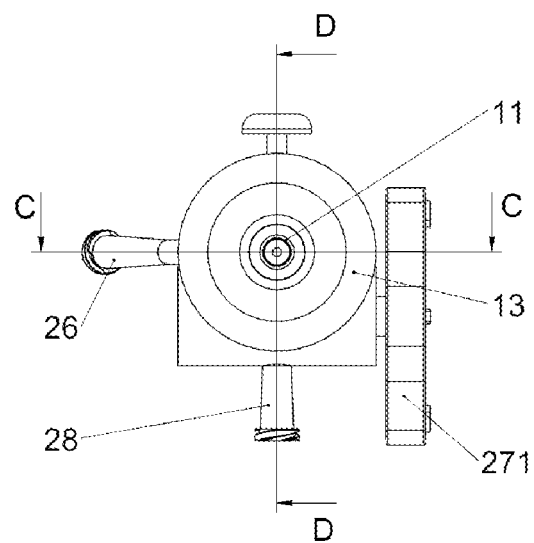
FIG. 6 is an axial diagram under a suction mode of the double-layer cryogenic inflatable balloon provided by the present invention.

Specifically, with reference to FIGS. 5 to 6, the three-pass cork valve 27 is a cork post 272 that has a radial cross-section with T-shaped communicated flow paths, the cork post 272 may be rotatably inserted into the cork chamber 238, and a contact surface between the cork post 272 and the cork chamber 238 is in a sealing state all the time. Since the gas return channel 233, the gas return joint 28 and the liquid-filling channel 234 are arranged in a T-shaped manner in the present embodiment, three paths in the cork post 272 are arranged in the T-shaped manner, so that the arrangement for the three flow paths in the cork post 272 should be adjusted correspondingly when the arrangement for the gas return channel 233, the gas return joint 28, and the liquid-filling channel 234 are adjusted, which is not limited here and may be adjusted according to actual situations.

Further, the cork post 272 is further connected with a handle 271 located outside the fluid-diverting cavity 23, and the cork post 272 is rotated by the handle 271 to achieve switching between channels.

Further, the handle is provided with an indication sign 239 for indicating the communication between the gas return channel 233 and the gas return joint 28, between the gas return joint 28 and the liquid-filling channel 234, and between the gas return channel 233 and the liquid-filling channel 234. For example, in FIGS. 10, 12 and 14, the indication sign 239 includes a fixed indication arrow on the fluid-diverting cavity 23, and an inflation indication arrow, a suction indication arrow, and a cryogenic indication arrow disposed on the handle 271.

In the process of rotating the handle 271, when the inflation indication arrow on the handle 271 is opposite to the fixed indication arrow, the gas return joint 28 is communicated with the liquid-filling channel 234; when the suction indication arrow on the handle 271 is opposite to the fixed indication arrow, the gas return channel 233 is communicated with the liquid-filling channel 234; when the cryogenic indication arrow on the handle 271 is opposite to the fixed indication arrow, the gas return channel 233 is communicated with the gas return joint 28.

The adjustment structure provided by the present embodiment has a simple structure, a smart design, and convenient operations; naturally, in other embodiments, the specific structure of the adjustment structure may be adjusted according to actual situations, which is not limited here.

In the present embodiment, the fluid-diverting cavity 23 is further provided with a pressure relief channel 237, wherein the pressure relief channel 237 has one end communicated with the gas return chamber 231, and has the other end protruding out of the fluid-diverting cavity 23 and inserted with a safety valve 29. When the gas return is blocked due to wrong adjustments of the modes of the three-pass cork valve 27 or other situations, a gas return pressure will be increased; when the gas return pressure reaches an initiating pressure of the safety valve 29, the safety valve is initiated, and the returned gas discharges the relieved pressure through a pressure relief channel 237 and the safety valve 29, wherein the initiating pressure of the safety valve 29 is higher than the gas return pressure in a normal cryogenic mode and is far below a maximum tolerance pressure of the cryogenic balloon 21.

In the present embodiment, the inflation assembly includes a gas bottle 4 and a gas bottle opening component 3, and the gas bottle 4 is connected to the gas inlet chamber 232 through the gas bottle opening component 3.

Figure 7:
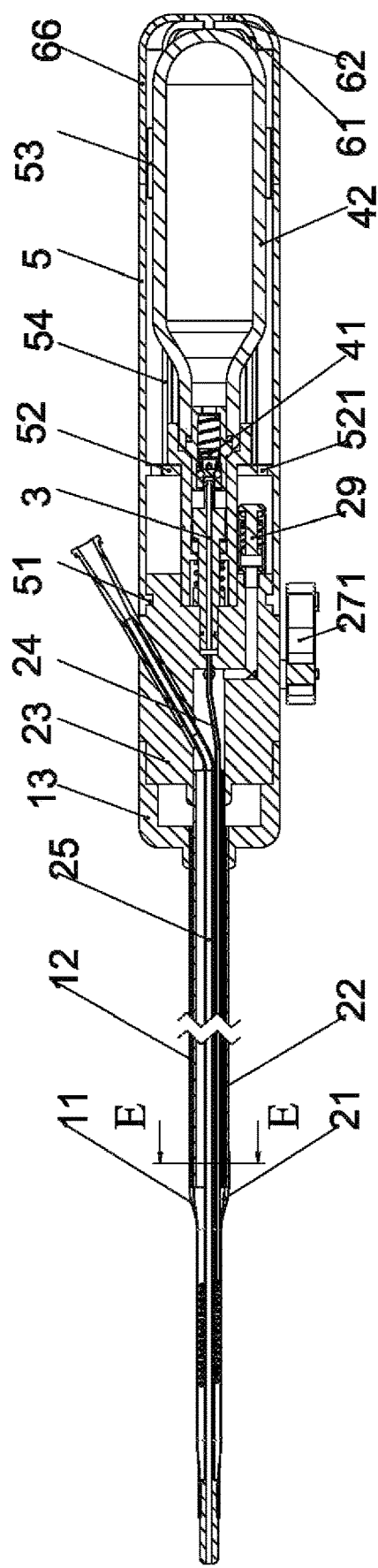
FIG. 7 is an axial cross-section diagram taken from C-C under the suction mode of the double-layer cryogenic inflatable balloon provided by the present invention.
Figure 8:
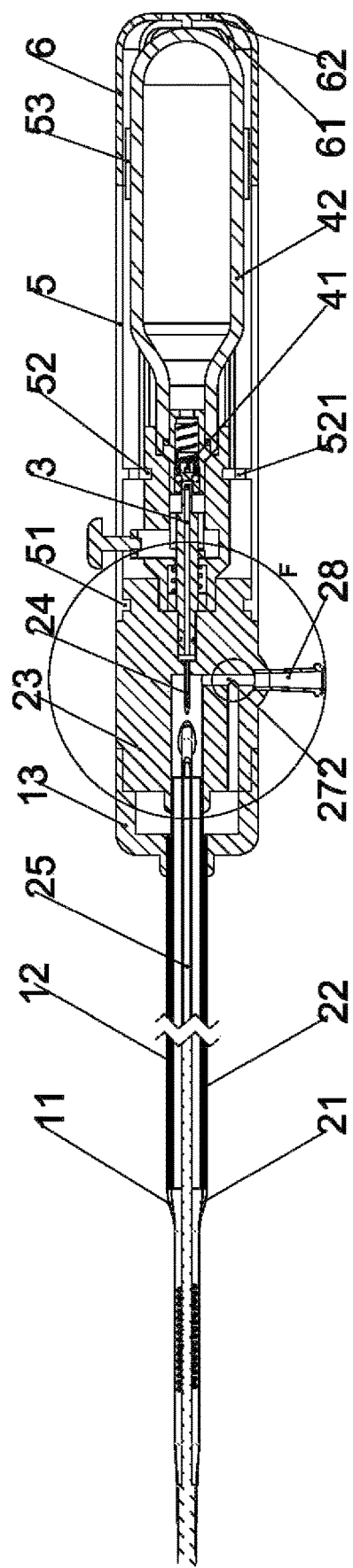
FIG. 8 is an axial cross-section diagram taken from D-D under the suction mode of the double-layer cryogenic inflatable balloon provided by the present invention.
Figure 9:
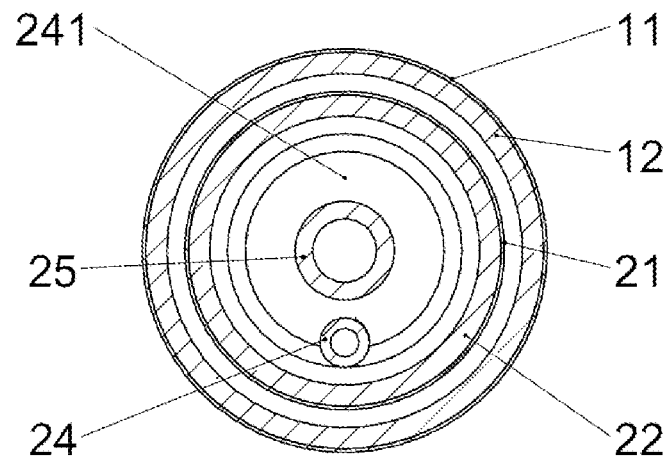
FIG. 9 is a radial cross-section diagram taken from E-E under the suction mode of the double-layer cryogenic inflatable balloon provided by the present invention.
Figure 10:
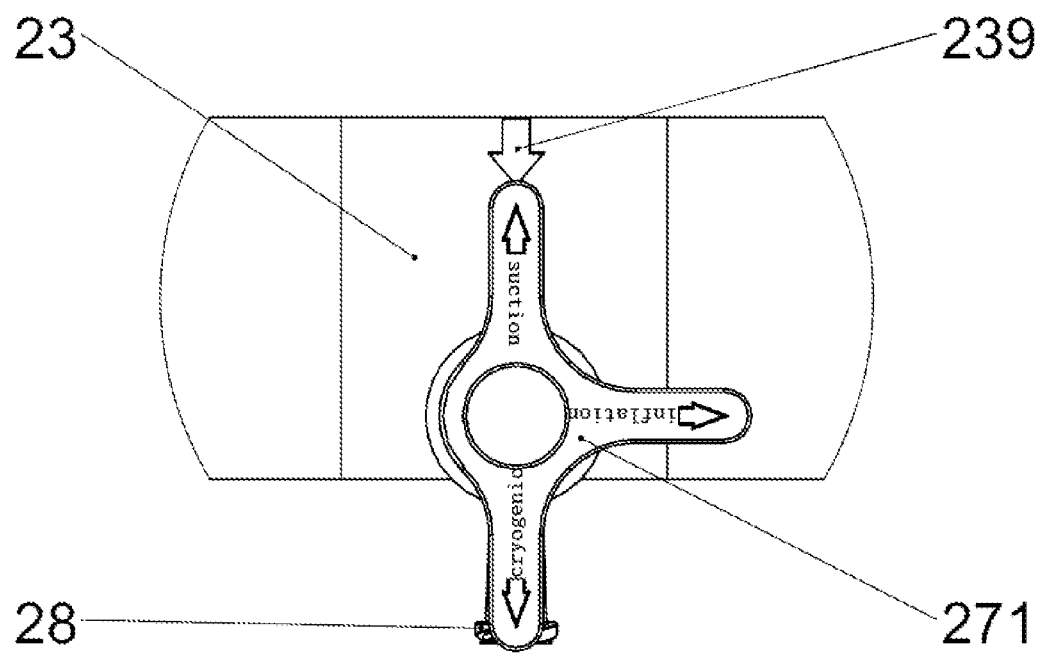
FIG. 10 is a diagram of a three-pass cork valve under a suction mode of the double-layer cryogenic inflatable balloon provided by the present invention.

Specifically, with reference to FIGS. 7 to 9, the gas bottle opening component includes a valve body 31, a hollow ejector pin 34 and a pushing rod assembly, and the valve body 31 has one end inserted into the gas inlet chamber 232 and the other end fixedly connected with a bottle mouth 42 of a gas bottle body 41, the valve body 31 being in sealed connection with the gas inlet chamber 232 and with the bottle mouth 42; the hollow ejector pin 34 is movably mounted in the valve body 31, with one end located in and communicating with the gas inlet chamber 232 and the other end abutting against a sealing mechanism in the bottle mouth 42; one end of the pushing rod assembly is connected with the hollow ejector pin 34, and may drive an axis of the hollow ejector pin 34 to move to eject off the sealing mechanism to be extended into the gas bottle body 41, so that the refrigerant gas in the gas bottle body 41 is input into the cryogenic balloon 21 through the hollow ejector pin 34, the gas inlet hole 235 and the gas inlet pipe 24.

In the present embodiment, the pushing rod assembly includes a button 32 and a pushing rod 33, wherein the pushing rod has one end passing through the valve body 31 to be fixedly connected with the hollow ejector pin 34, and has the other end protruding out of the casing assembly 5 to be connected with the button 32. The button 32 is pushed such that the hollow ejector pin 34 is driven to move axially by the pushing rod 33.

In the present embodiment, the inflation assembly is mounted on the fluid-diverting cavity 23 through the casing assembly 5. Specifically, the casing assembly includes a left semi-casing 501 and a right semi-casing 502 that are covered on the inflation assembly symmetrically in the radial direction, and includes a rear lid 6 covering on a side of the inflation assembly deviated from the fluid-diverting cavity 23.

The left semi-casing 501 is connected with the right semi-casing 502 by structures such as snap buckles, screws, etc. so as to cover an outer side of the inflation assembly, and the position where the left semi-casing 501 is connected with the right semi-casing 502 is in the sealing state to prevent the exhaust gas from overflowing. Ends of the left semi-casing 501 and the right semi-casing 502 after being connected with each other are provided internally with a limiting ring 51, a rear end of the fluid-diverting cavity 23 is provided with a limit groove correspondingly, and the left semi-casing 501 and the right semi-casing 502 are engaged into the limiting groove through the limiting ring 51 to be in a limited connection with the fluid-diverting cavity 23; the rear lid 6 is screwed to a thread portion 53 on the other ends of the left semi-casing 501 and the right semi-casing 502 to achieve connection.

Further, inner side walls of the left semi-casing 501 and the right semi-casing 502 are provided with a limiting plate 52 snapped on the gas bottle opening component (i.e., the valve body 31), and the limiting plate 52 limits the gas bottle opening component axially and radially at the same time.

Further, the inner side walls of the left semi-casing 501 and the right semi-casing 502 are provided with a reinforcing rib 56, and an inner wall of the rear lid 6 is provided with a reinforcing rib 61; the provisions of the reinforcing rib 56 and the reinforcing rib 61 are used to enhance the strength of the casing assembly 5 and the rear lid 6, and the casing assembly 5 and the rear lid 6 are separated from the gas bottle for exhausting the gas. Further, the casing assembly 5 and the rear lid 6 are further provided with a vent hole 521 and a vent hole 62; the gas exhausted or leaked from the gas bottle opening component 3 or the safety valve 29 is discharged through the vent hole 521, a gap between the casing 5 and the gas bottle 42, a gap of the thread portion 53, a gap between the rear lid 6 and the gas bottle 42 as well as the vent hole 62 in sequence.

In the present embodiment, the double-layer cryogenic inflatable balloon further includes a wire guiding pipe 25, which penetrates through the cryogenic balloon 21, the inner catheter 22, the liquid-filling chamber 14 and the gas return chamber 231; one end of the wire guiding pipe (i.e., a wire guiding pipe head 251) extends into the cryogenic balloon 21 while being connected with the front ends of the cryogenic balloon 21 and the inflatable balloon 11, and the other end of the wire guiding pipe (i.e., a wire guiding outlet 26) is drawn from a wire guiding hole 236 on the fluid-diverting cavity 23. In the present embodiment, through the provision of the wire guiding pipe 13, the wire extends into the wire guiding pipe 25 through the wire guiding outlet 26 and extends to the wire guiding pipe head 251 when in use, so that the balloon is sent to a stenosis area to be treated along a wire path.

Naturally, in other embodiments, the provision of the wire guiding pipe 13 may also be eliminated, which is not limited here.

Figure 11:
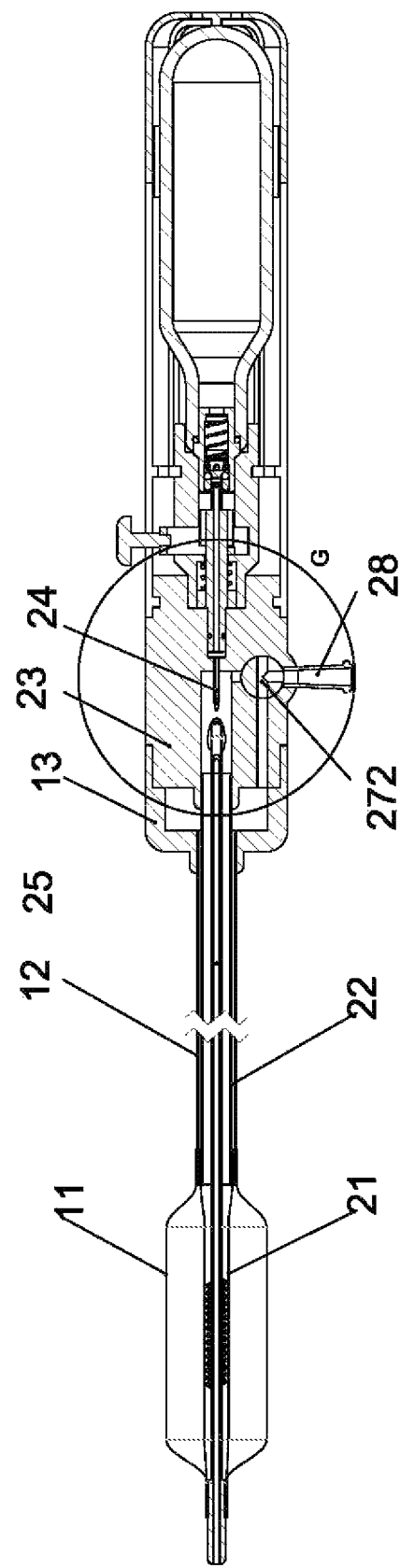
FIG. 11 is an axial cross-section diagram under an inflation mode of the double-layer cryogenic inflatable balloon provided by the present invention.
Figure 12:
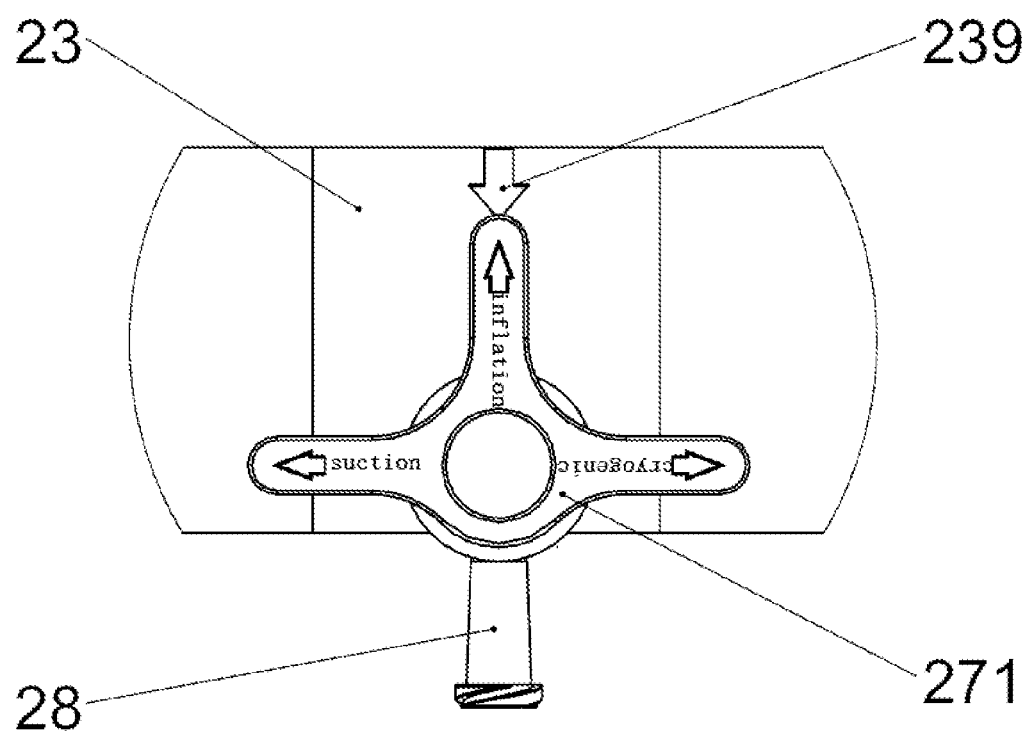
FIG. 12 is a diagram of a three-pass cork valve under the inflation mode of the double-layer cryogenic inflatable balloon provided by the present invention.
Figure 13:
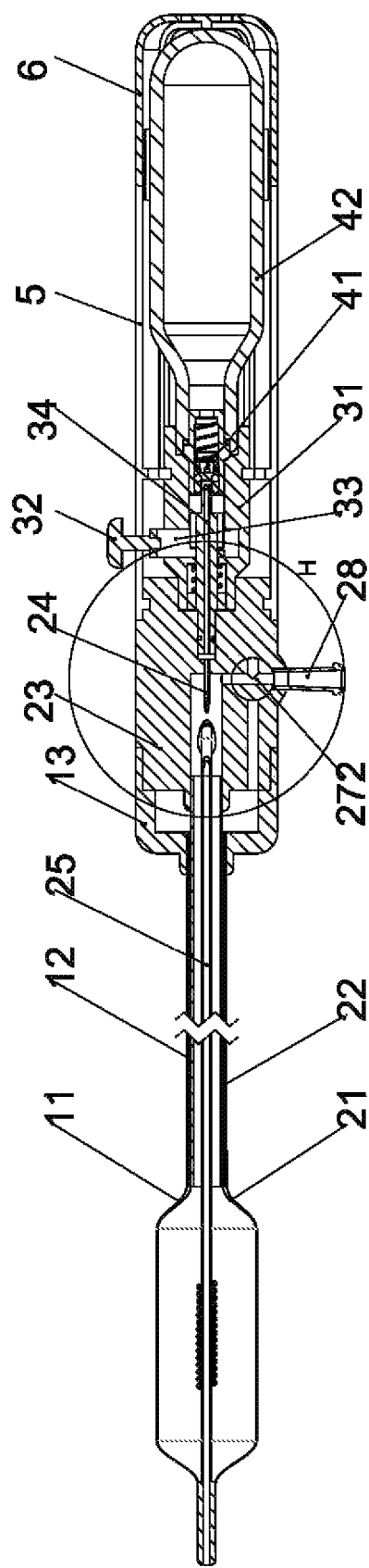
FIG. 13 is an axial cross-section diagram under a cryogenic mode of the double-layer cryogenic inflatable balloon provided by the present invention.
Figure 14:
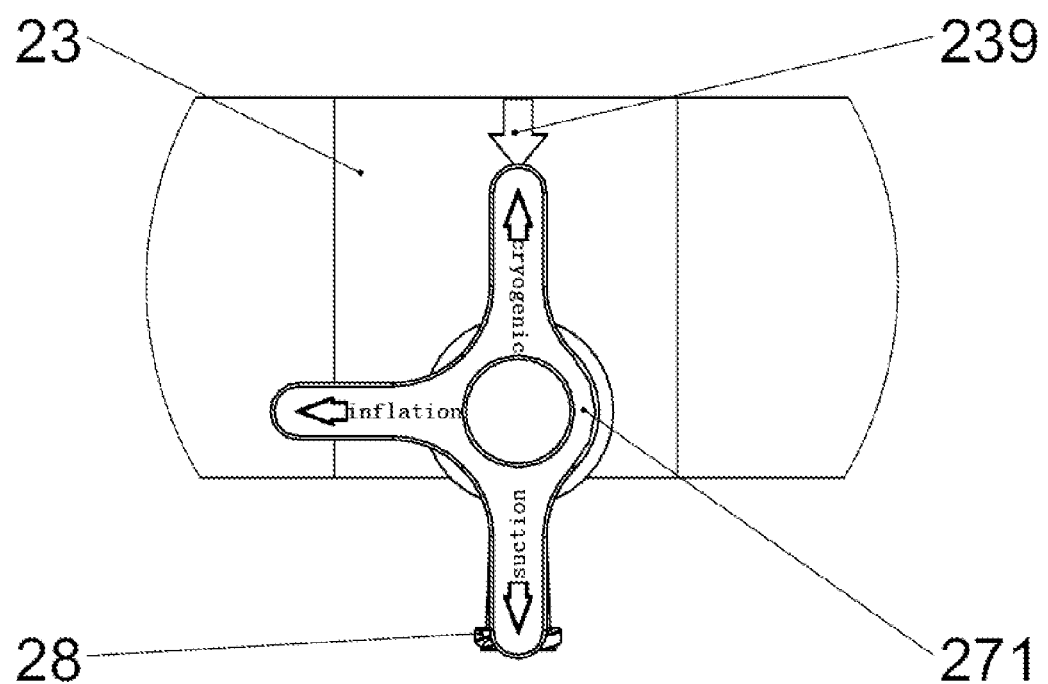
FIG. 14 is a diagram of the three-pass cork valve under the cryogenic mode of the double-layer cryogenic inflatable balloon provided by the present invention.

The working process of the double-layer cryogenic inflatable balloon provided by the present invention is further described as below, specifically:

With reference to FIGS. 11 to 12, after reaching lesions by an introduction method such as using an endoscope, the inflatable balloon 11 is placed on a stenosis segment, the handle 271 is adjusted to an inflatable mode, and then the gas return 28 is not communicated with the gas return pipe 233 and the gas return joint 28 is communicated with the liquid-filling channel 234, i.e., the cryogenic balloon assembly 2 is separated from the outside world and the inflatable balloon component 1 is communicated with the liquid-filling gun. The saline is injected into the inflatable balloon 11 through the gas return joint 28, the cork post 272, the liquid-filling pipe 234, an internal portion of the liquid-filling cavity 13 and the gap between the outer catheter 12 and the inner catheter 22 in sequence by the liquid-filling gun, and then the inflatable balloon 11 begins to inflate and a pressure gauge on the liquid-filling gun will indicate the liquid-filling pressure, wherein a certain liquid-filling pressure corresponds to a corresponding diameter of the inflatable balloon 11; after the inflation, the saline in the inflatable balloon component 1 is drained through the liquid-filling gun;

with reference to FIGS. 13 to 14, after the saline in the inflatable balloon 11 is drained, the inflatable balloon 11 adheres to the cryogenic balloon 21, and the handle 271 is adjusted to a cryogenic mode while removing the liquid-filling gun, and then the gas return 28 is communicated with the gas return pipe 233 and the gas return joint 28 is not communicated with the liquid-filling channel 234, i.e., the cryogenic balloon assembly 2 is open to the outside world and the inflatable balloon component 1 is separated from the outside world. The button 32 is pressed so that the button 32 drives the pushing rod 33 to move radially, the radial movement of the pushing rod 33 drives the ejector pin 34 to move backward axially, and the hollow ejector pin 34 ejects off the sealing mechanism in the gas bottle mouth 41, so that the refrigerant in the gas bottle body 42 passes through the gas bottle mouth 41, an internal portion of the hollow ejector pin 34, the gas inlet pipe 24 and the spiral gas inlet pipe 241 in sequence, and finally is sprayed out to the internal portion of the cryogenic balloon 21 from the gas outlet hole 242; the refrigerant will perform throttle cooling through Joule-Thompson Effect and inflate the cryogenic balloon 21, and the throttle-liquefied refrigerant is sprayed to an inner surface of the cryogenic balloon 21 to absorb the heat and to be evaporated; through the thermal conduction of the cryogenic balloon 21 and the inflatable balloon 11, the tissues of the narrow segment are frozen, and the evaporated refrigerant gas is discharged through the inner catheter 22, the gas return chamber 231, the gas return pipe 233, the cork post 272 and the gas return joint 28.

Those skilled in the art should understand that the present invention may be realized in many other concrete forms without departing from its own spirit or scope. Although the embodiment of the present invention has been described, it should be understood that the present invention should not be limited to these embodiments, and those skilled in the art may make changes and modifications within the spirit and scope of the present invention as defined in the attached claims.

What is claimed is:

1. A double-layer cryogenic inflatable balloon, comprising:
an inflatable balloon assembly, comprising an inflatable balloon, an outer catheter, and a liquid-filling cavity, the liquid-filling cavity being provided with a liquid-filling chamber, the inflatable balloon being communicated with the liquid-filling chamber through the outer catheter;
a cryogenic balloon assembly, comprising a cryogenic balloon, an inner catheter, a fluid-diverting cavity, a gas inlet pipe, and an inflation assembly, the cryogenic balloon being located in the inflatable balloon, the inner catheter being located in the outer catheter, the fluid-diverting cavity being provided with a gas return chamber, the cryogenic balloon being communicated with the gas return chamber through the inner catheter;

wherein the fluid-diverting cavity is further provided with a gas return channel, a liquid-filling channel and a cork chamber, the gas return channel having one end communicated with the gas return chamber and the other end communicated with the cork chamber; the liquid-filling channel has one end communicated with the cork chamber and the other end communicated with the liquid-filling chamber; the cork chamber is communicated with a gas return joint, and is internally provided with an adjustment structure for achieving connection and disconnection between the gas return channel and the gas return joint, between the gas return joint and the liquid-filling channel and between the gas return channel and the liquid-filling channel;

the fluid-diverting cavity is further provided with a gas inlet chamber, and the gas inlet pipe penetrates through the cryogenic balloon, the inner catheter and the fluid-diverting cavity, the gas inlet pipe having one end located in the cryogenic balloon and the other end communicated with the gas inlet chamber; the gas inlet chamber is further communicated with the inflation assembly, and the inflation assembly is used to input a refrigerant gas into the cryogenic balloon through the gas inlet chamber and the gas inlet pipe.

2. The double-layer cryogenic inflatable balloon according to claim 1, wherein the liquid-filling cavity is disposed on an end of the fluid-diverting cavity facing towards the inner catheter, the end of the fluid-diverting cavity facing towards the inner catheter is provided with the gas return chamber, and the inner catheter extends out of the outer catheter to pass through the liquid-filling chamber and is then communicated with the gas return chamber.

3. The double-layer cryogenic inflatable balloon according to claim 2, wherein the gas inlet chamber is disposed on an end of the fluid-diverting cavity deviated from the inner catheter, a gas inlet hole is disposed between the gas inlet chamber and the gas return chamber, the other end of the gas inlet pipe extends out of the inner catheter to pass through the liquid-filling chamber and the gas return chamber in sequence and is then in sealed connection with the gas inlet hole.

4. The double-layer cryogenic inflatable balloon according to claim 3, wherein the end of the gas inlet pipe located in the cryogenic balloon is connected with a spiral gas inlet pipe, and at least one gas outlet hole is formed in the spiral gas inlet pipe.

5. The double-layer cryogenic inflatable balloon according to claim 4, wherein the at least one gas outlet hole includes a plurality of the gas outlet holes that are formed uniformly in the spiral gas inlet pipe in an axial direction and a radial direction thereof.

6. The double-layer cryogenic inflatable balloon according to claim 3, wherein the inflation assembly comprises a gas bottle and a gas bottle opening component, and the gas bottle is connected to the gas inlet chamber through the gas bottle opening component.

7. The double-layer cryogenic inflatable balloon according to claim 6, wherein the gas bottle opening component comprises a valve body, a hollow ejector pin and a pushing rod assembly, and the valve body has one end connected to the gas inlet chamber and the other end connected with a bottle mouth of the gas bottle; the hollow ejector pin is movably mounted in the valve body, with one end located in the gas inlet chamber and the other end abutting against a sealing mechanism in the bottle mouth; one end of the pushing rod assembly is connected with the hollow ejector pin, and is configured to drive an axis of the hollow ejector pin to move to eject off the sealing mechanism to extend into the gas bottle.

8. The double-layer cryogenic inflatable balloon according to claim 7, wherein the inflation assembly is mounted on the fluid-diverting cavity through a casing assembly.

9. The double-layer cryogenic inflatable balloon according to claim 8, wherein the casing assembly comprises a left semi-casing and a right semi-casing that are covered on the inflation assembly symmetrically in a radial direction, and a rear lid covering on a side of the inflation assembly deviated from the fluid-diverting cavity; each of the left and right semi-casings has a first end and a second end; the first ends of the left semi-casing and the right semi-casing are connected onto the fluid-diverting cavity, and the rear lid is connected onto the second ends of the left semi-casing and the right semi-casing.

10. The double-layer cryogenic inflatable balloon according to claim 9, further including a limiting plate clamped on the gas bottle opening component, wherein each of the left semi-casing and the right semi-casing includes an inner side wall, and wherein the limiting plate is mounted to at least one of the inner side walls of the left semi-casing and the right semi-casing.

11. The double-layer cryogenic inflatable balloon according to claim 9, wherein the rear lid covering is provided with a vent hole.

12. The double-layer cryogenic inflatable balloon according to claim 1, wherein the adjustment structure is of a three-pass cork valve, and the three-pass cork valve is configured to achieve the connection and disconnection between the gas return channel and the gas return joint and between the gas return joint and the liquid-filling channel.

13. The double-layer cryogenic inflatable balloon according to claim 12, wherein a cork post is further connected with a handle for driving the cork post to rotate, and the handle is provided with an indication sign for indicating the connection between the gas return channel and the gas return joint, between the gas return joint and the liquid-filling channel and between the gas return channel and the liquid-filling channel.

14. The double-layer cryogenic inflatable balloon according to claim 1, wherein the fluid-diverting cavity is further provided with a pressure relief channel, and the pressure relief channel has one end communicated with the gas return chamber and the other end extending out of the fluid-diverting cavity and provided with a safety valve.

15. The double-layer cryogenic inflatable balloon according to claim 1, further comprising a wire guiding pipe that penetrates through the cryogenic balloon, the inner catheter, the liquid-filling chamber and the gas return chamber; each of the cryogenic balloon and the inflatable balloon has a front end, one end of the wire guiding pipe extends into the cryogenic balloon while being connected with the front ends of the cryogenic balloon and the inflatable balloon, and the other end of the wire guiding pipe is configured to be extracted from a wire guiding hole in the fluid-diverting cavity.

16. The double-layer cryogenic inflatable balloon according to claim 1, wherein the end of the gas inlet pipe located in the cryogenic balloon is connected with a spiral gas inlet pipe, and a gas outlet hole is formed in the spiral gas inlet pipe.

17. The double-layer cryogenic inflatable balloon according to claim 1, wherein the inflation assembly comprises a gas bottle and a gas bottle opening component, and the gas bottle is connected to the gas inlet chamber through the gas bottle opening component.

\* \* \* \* \*